(12) United States Patent
Martin (10) Patent No.: US 11,045,210 B2
(45) Date of Patent: Jun. 29, 2021

(54) FLEXIBLE SPINAL DRIVER OR DRILL WITH A MALLEABLE CORE, AND/OR FIXED CORE RADIUS

(71) Applicant: DePuy Synthes Products, Inc., Raynham, MA (US)

(72) Inventor: Thomas Martin, Riverside, RI (US)

(73) Assignee: DePuy Synthes Products, Inc., Raynham, MA (US)

(*) Notice: Subject to any disclaimer, the term of this patent is extended or adjusted under 35 U.S.C. 154(b) by 517 days.

(21) Appl. No.: 14/481,838

(22) Filed: Sep. 9, 2014

(65) Prior Publication Data

US 2015/0374418 A1 Dec. 31, 2015

Related U.S. Application Data

(60) Provisional application No. 62/017,596, filed on Jun. 26, 2014.

(51) Int. Cl.
*A61B 17/16* (2006.01)
*A61B 17/88* (2006.01)
*A61B 17/70* (2006.01)
*A61B 17/80* (2006.01)
*A61B 17/00* (2006.01)

(52) U.S. Cl.
CPC ...... *A61B 17/1631* (2013.01); *A61B 17/1615* (2013.01); *A61B 17/1671* (2013.01); *A61B 17/7059* (2013.01); *A61B 17/7074* (2013.01); *A61B 17/7082* (2013.01); *A61B 17/808* (2013.01); *A61B 17/8057* (2013.01); *A61B 17/8875* (2013.01); *A61B 2017/00464* (2013.01); *A61B 2017/00867* (2013.01); *A61B 2017/00871* (2013.01); *A61B 2017/00946* (2013.01)

(58) Field of Classification Search
CPC ............ A61B 17/1631; A61B 17/1642; A61B 17/1671
See application file for complete search history.

(56) References Cited

U.S. PATENT DOCUMENTS

| 8,366,559 | B2 | 2/2013 | Papenfuss | |
| 9,078,740 | B2* | 7/2015 | Steiner | A61B 17/8875 |
| 2011/0319896 | A1* | 12/2011 | Papenfuss | A61B 17/1631 606/79 |
| 2012/0150301 | A1 | 6/2012 | Gamache | |

FOREIGN PATENT DOCUMENTS

| GB | 2250441 | 6/1992 |
| WO | WO 2011080104 | 7/2011 |

* cited by examiner

*Primary Examiner* — Andrew Yang

(57) ABSTRACT

The improvement is a spinal instrument (preferably, a bone screw driver) having a flexible shaft comprising a plurality of interlocking segments carried on a malleable core rod. The flexible shaft allows a screwdriver handle to be perfectly in-line with the cage inserter if desired, while still taking advantage of the tactile feel and torque transmission of the flex segment in its bent position. Accordingly, a surgeon can limit the amount of retraction and keep the driver handle close to the inserter without having to overcome the forces of the flexible segments' natural straight configuration.

16 Claims, 9 Drawing Sheets

FLEXIBLE SPINAL DRIVER OR DRILL WITH A MALLEABLE CORE, AND/OR FIXED CORE RADIUS

CONTINUING DATA

This application claims priority from application U.S. Ser. No. 62/017,596, filed Jun. 26, 2014, entitled "Flexible Spinal Driver or Drill with a Malleable Core, and or Fix Core Radius", Martin, the specification of which is incorporated by reference in its entirety.

BACKGROUND OF THE INVENTION

When performing a spinal procedure such as an anterior cervical discectomy and fusion (ACDF), the surgeon often has a number of implant options that may achieve the desired clinical outcomes of disc height maintenance and pain relief. Because of their clinical benefits, zero-profile fusion cages that accept bone anchors and are secured to the adjacent anatomy have experienced an increased usage and adoption in the ACDF procedure. These cages typically have angled bone anchors (such as screws) that pass through a portion of the cage's anterior wall and into the adjacent vertebral endplates.

However, if a surgeon were to choose a low profile, stand-alone fusion device (such as a fixation cage comprising one or more bone screws), there remains a surgical technique challenge associated with the insertion of the screws. Traditionally, an instrument having a straight shaft is used to insert the screws through the cage at the steep angle to ensure bone penetration. However, screw insertion with a straight-shaft instrument at locations up near a patient's chin or sternum produces some challenging approach angles. Recently, there have been improvements to the insertion instrument that help facilitate screw placement at these difficult approach angles. Some of these improvements include the adoption of universal joints and flexible inserter instruments that allow for torque transmission while still positioning their handles off-axis from the trajectory of the screw. For example, some flexible inserter instruments achieve flexibility by possessing a plurality of interlocking segments just proximal of their distal working tip. Once the tip of such a flexible driver is inserted into the drill guide, the handle of the driver can be repositioned to the desired location and torque can be transmitted to advance the screw.

However, one of the challenges associated with this flexible technology is that the flexible shaft is typically straight in its resting configuration. Accordingly, one of two procedures needs to be carried out. In a first procedure, the amount of soft tissue retraction has to temporarily be increased in order to engage the tip of the driver into the drill guide and once engaged, the soft tissue retraction can be minimized again and the handle can be held in a desirable position, such as near parallel to the implant inserter. In a second procedure, the tip can be inserted into the drill guide at a less steep angle than the screw trajectory (but not perfectly parallel to the inserter) and the spring force of the flex segment has to be overcome in order for the tip to find the drill guide trajectory. Upon this "turning the corner" step, as a downforce is provided, the self-retention of the screw may become disengaged.

US Published Patent Application No. 2012-0150301 (Gamache) discloses a flexible bone screw driver comprising: a) a proximal handle, b) an intermediate shaft, c) a flexible distal end portion comprising a plurality of interlocking segments portion and a distal tip adapted to engage a screw head, and d) a pre-bent sleeve that is placed over and around the plurality of interlocking segments, wherein the plurality of interlocking segments portion is substantially straight in its unloaded configuration.

SUMMARY OF THE INVENTION

Figure 1:
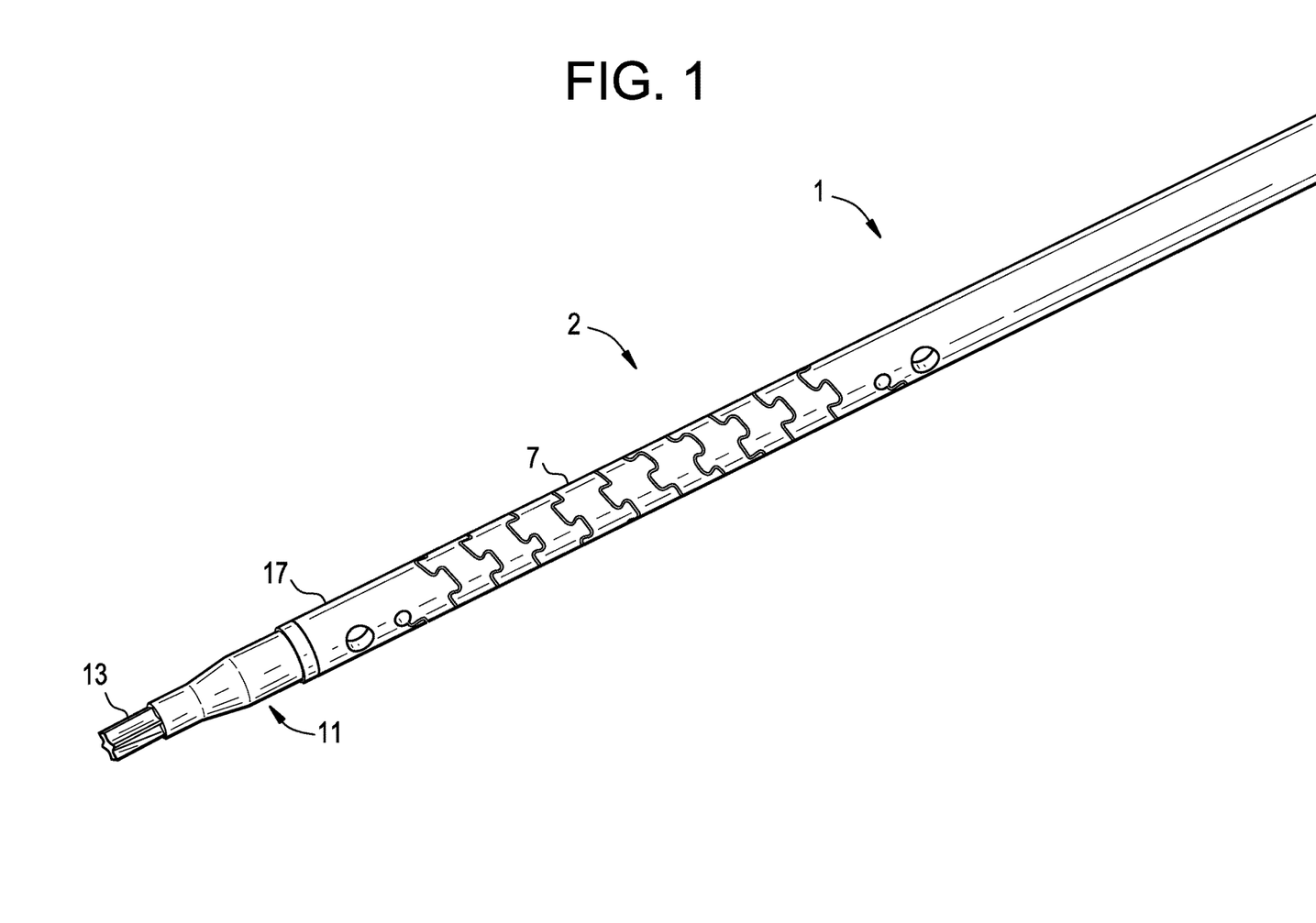
FIG. 1 discloses a perspective view of a portion of the driver of the present invention.
Figure 2:
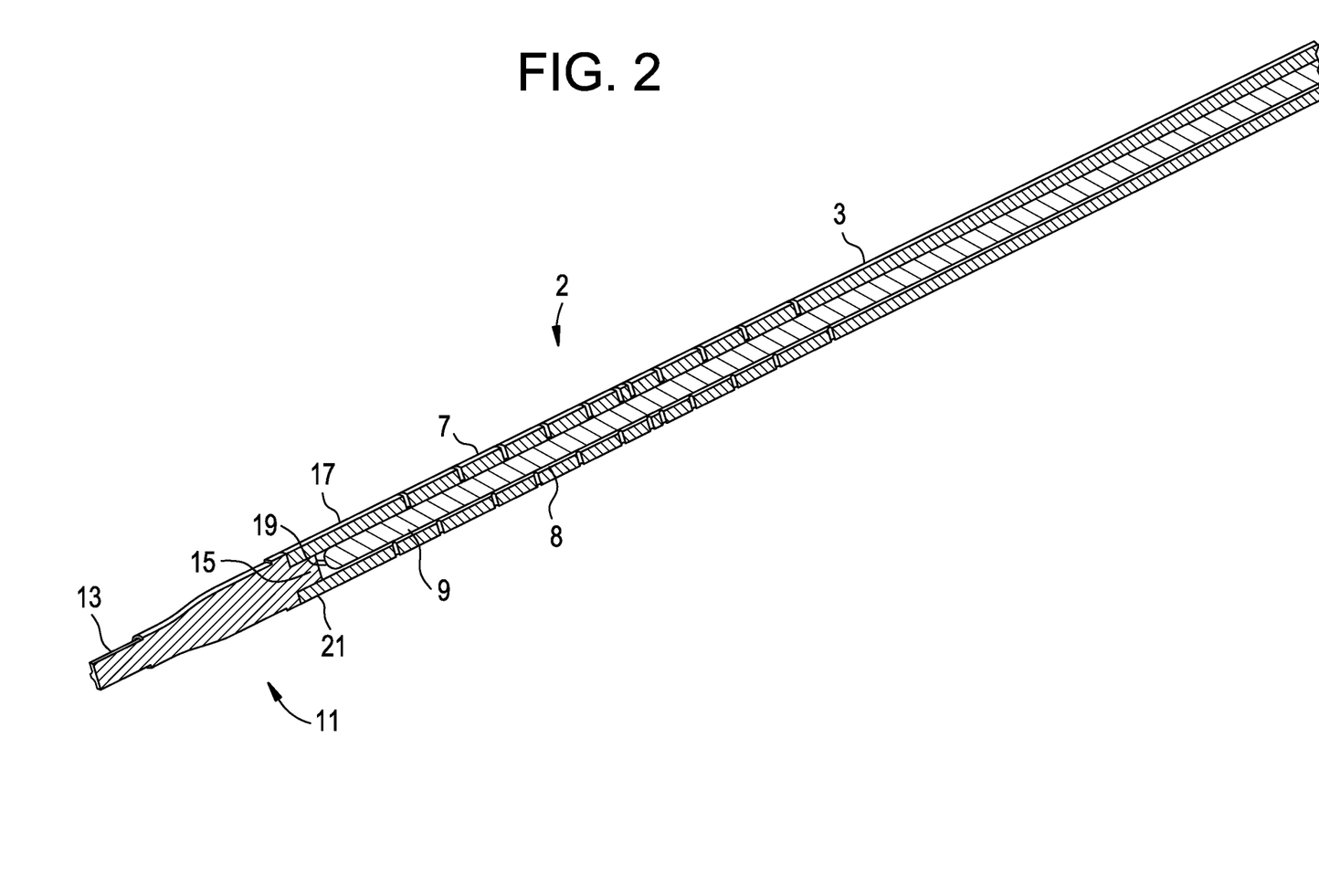
FIG. 2 discloses a cross-sectional view of a portion of the driver of the present invention.
Figure 3:
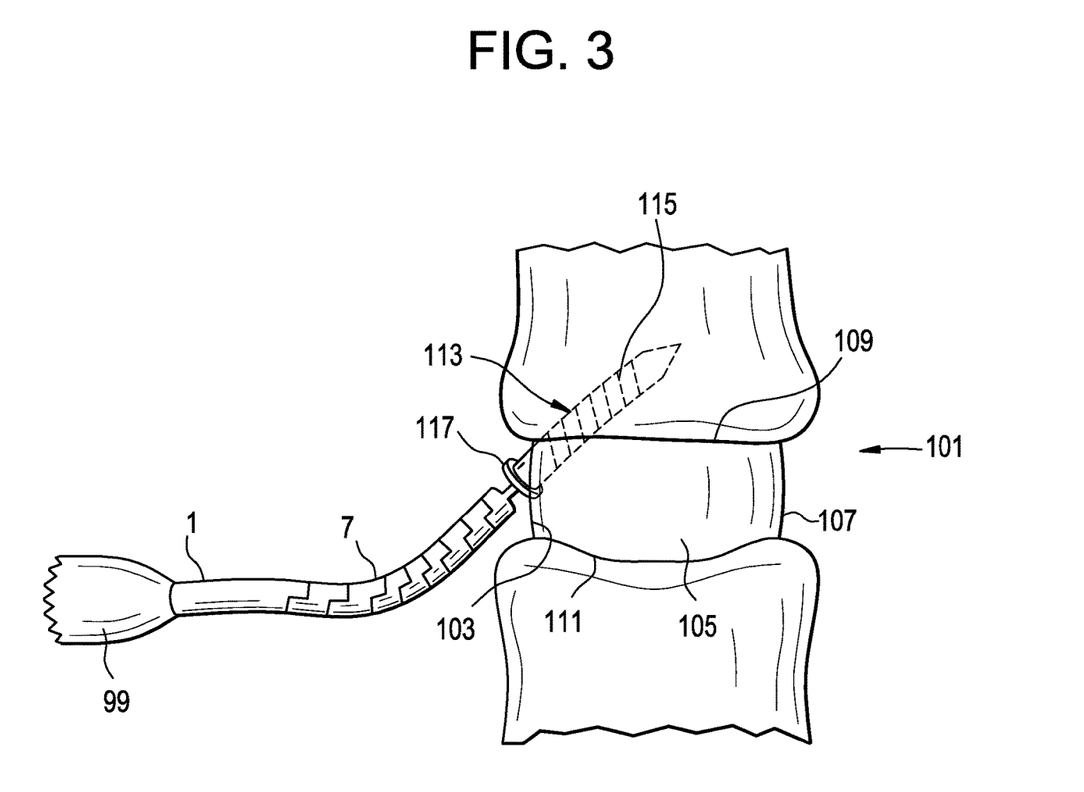
FIG. 3 discloses the driver of the present invention driving a screw into a fusion cage implanted between vertebral bodies.

In order to overcome the issues discussed above, in one aspect of the present invention, and now referring to FIGS. 1-3, there is provided an improvement on the flexible shaft technology that has benefits for the patient and the surgeon. The improvement is a bone screw driver having a flexible shaft comprising a plurality of interlocking segments carried on a flexible core rod. The flexible shaft allows a screwdriver handle to be perfectly in-line with the cage inserter if desired, while still taking advantage of the tactile feel and torque transmission of the flex segment in its bent position. Accordingly, a surgeon can limit the amount of retraction and keep the driver handle close to the inserter without having to overcome the forces of the flexible segments' natural straight configuration. The flexible driver can have geometries that allow for flexing, attachment (snapping-on to a drill), and easy cleaning, if desired.

Therefore, in accordance with the present invention, there is provided a flexible spinal instrument comprising:
a) a proximal portion adapted for connection to a handle or a drill,
b) an intermediate shaft comprising:
  i) a plurality of interlocking segments, each segment having a throughhole, and
  ii) a malleable rod extending through the throughhole of each segment, and
c) a distal portion having a working tip.

Preferably, the instrument has a first substantially linear configuration and a second deformed configuration, wherein the second deformed configuration allows rotation of the shaft and an application of force along an axis of the working tip.

Also in accordance with the present invention, there is provided an assembly comprising:
a) a spinal implant comprising a at least one threaded throughhole,
b) a bone screw received in the threaded throughhole, the bone screw having a threaded shaft and a proximal head,
c) the spinal instrument of claim 1,
wherein the distal tip of the inserter is received in the proximal head of the bone screw,
wherein the first bone screw extends through the top surface of the cage.

DETAILED DESCRIPTION OF THE INVENTION

Now referring to FIGS. 1-3, there is provided a flexible bone screw driver comprising:
  a) a rigid proximal portion 1 adapted for connection to a handle 99 or a drill,
  b) an intermediate shaft 2 comprising:
    i) a plurality of interlocking segments 7, each segment having a throughhole 8, and
    ii) a malleable rod 9 extending through the throughhole of each segment, and
  c) a distal portion 11 having a working tip 13,
wherein the proximal portion is connected to the intermediate shaft, and
wherein the distal portion of the driver is connected to the intermediate shaft.

The distal portion of the driver has a distal working tip and a proximal connection portion 15. In general, the working tip is adapted to perform a function on a workpiece via rotation. In some embodiments, the working tip of the driver is adapted to insert bone screws. In others, the working tip of the driver is adapted to drill pilot holes. Preferably, the proximal connection portion is adapted for secure attachment to the distal-most 17 of the interlocking segments. The distal portion of the driver is generally made of a rigid material such as metals or certain plastics.

The malleable rod can be made of any biocompatible material that will maintain the desired flexible shape. In some embodiments, the flexible rod can be made from a malleable material selected from the group consisting of a polymer or a memory metal (such as nitinol). The selection of the material and rod diameter should be such that the rod can be flexed to any angle between about 0 degrees and 180 degrees. The malleable rod can be fixed to the proximal and distal portions of the driver, or can float therebetween. When the malleable rod floats within the plurality of interlocking segments, this allows for its easy removal for cleaning. In some embodiments, the malleable rod is substantially straight in its unloaded condition. In others, the malleable rod carries has a pre-bent angle in its unloaded condition, thereby pre-determining the trajectory of the tip and facilitating the appropriate and desired insertion angle of the screw into the drill guide without increasing the amount of tissue retraction. In some embodiments, the malleable rod has a distal bearing surface for rotating the outer section of the driver or drill.

The interlocking segments can be made of any biocompatible material that will maintain the desired shape. This can include metals or certain plastics. In some embodiments, there are between about five and fifteen interlocking segments in the intermediate shaft. In this range, these segments together allow for the desired smooth bending while retaining simplicity. Each interlocking segments has a throughhole adapted for reception of the malleable rod, so that when the interlocking segments are joined, the malleable rod can slide within the series of interlocking segments. The distal-most 17 of the interlocking segments should be adapted for secure attachment to the distal portion of the driver. In some embodiments thereof, the distal-most of the interlocking segments has a tubular distal end 21 that friction_fits over the proximal connection portion of the distal portion of the driver.

In some embodiments, the driver has a rigid proximal portion 1 that is adapted for connection to a handle. This connection may be permanent or releasable. This allows the surgeon to use the driver manually as a screwdriver. In some embodiments, the driver has a proximal portion that is adapted for connection to a port on a power drill. This allows the surgeon to power the driver via the rotary power supplied by the drill.

Now referring to FIG. 3, there is provided an assembly comprising:
  a) a spinal implant comprising at least one threaded throughhole (preferably a fusion cage 101 comprising a front wall 103, a pair of opposing side walls 105, a back wall 107, and top 109 and bottom 111 surfaces adapted for gripping opposed vertebral endplates, wherein the front wall comprises at least one threaded throughhole),
  b) a bone screw received in the threaded throughhole, the bone screw having a threaded shaft 115 and a proximal head 117,
  c) the driver of the present invention,
  wherein the distal tip of the inserter is received in the proximal head of the bone screw,
wherein the first bone screw extends through the top surface of the cage.

Figure 4:
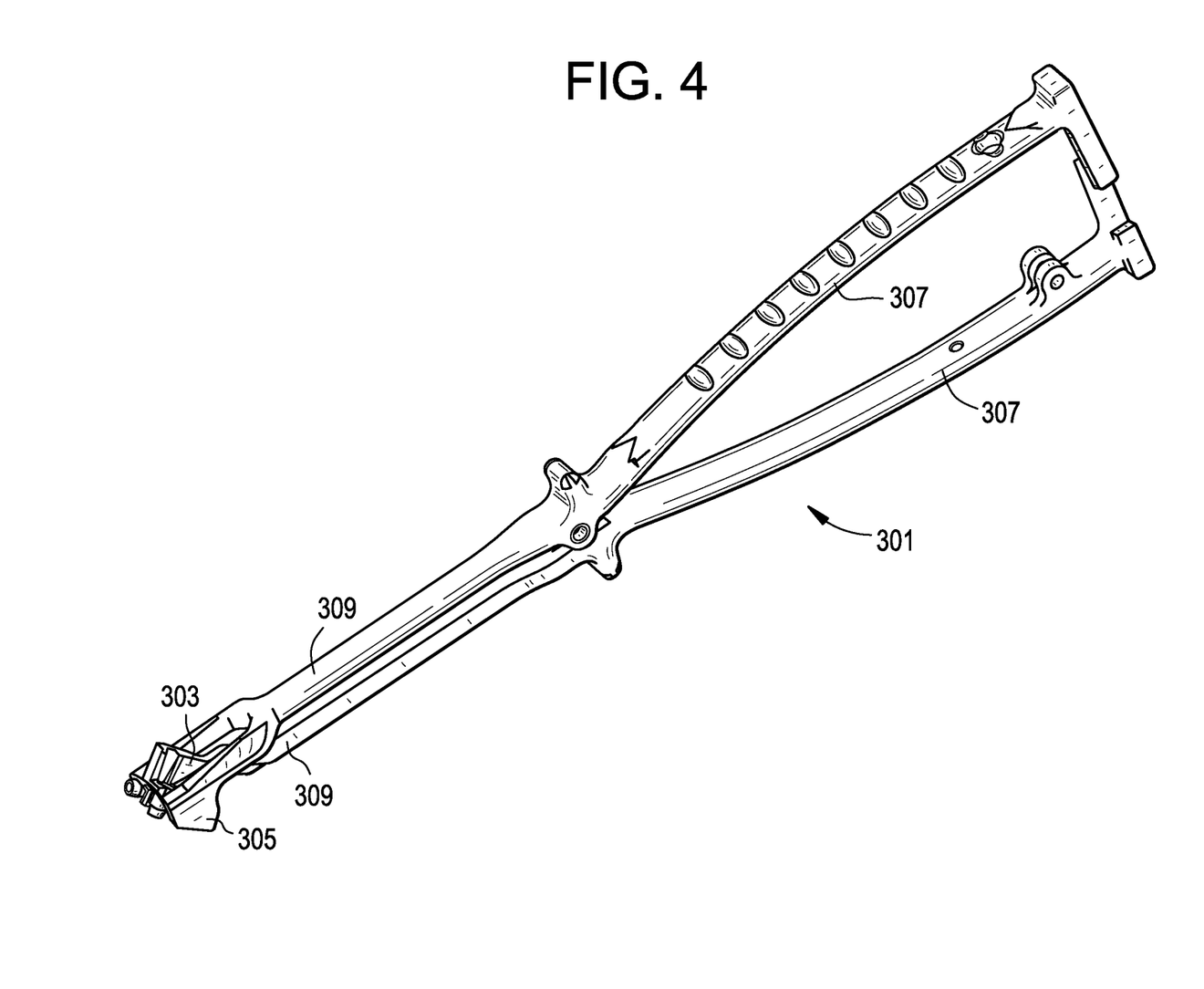
FIGS. 4-6 disclose embodiments involving a preferred instrument for holding the driver of the present invention.
Figure 5:
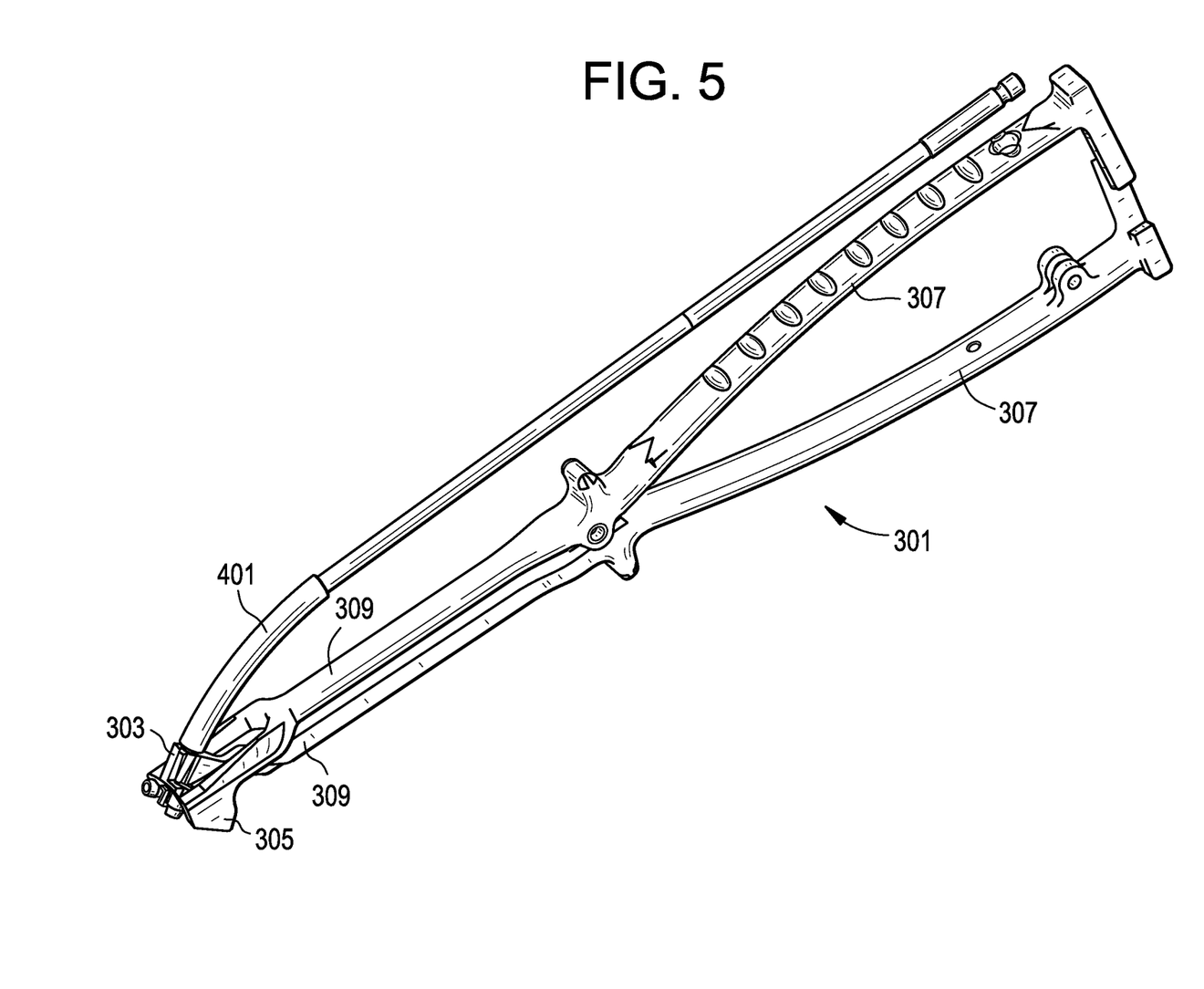
Figure 6:
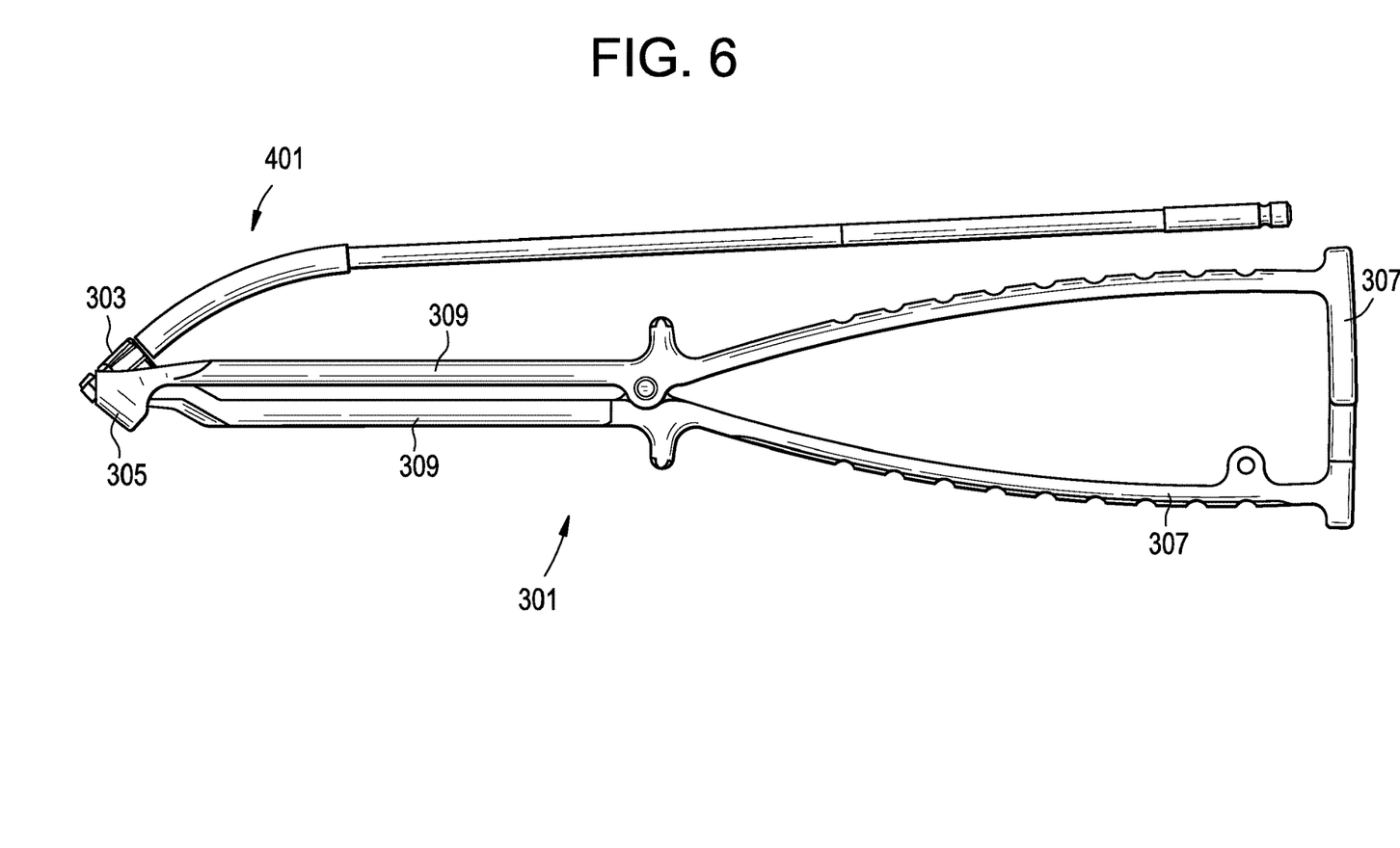

Now referring to FIGS. 4-6, there is provided an insertion instrument 301 for holding the driver of the present invention. The distal portion of jaw 305 of this instrument includes a receiver 303 that receives the working tip of the driver of the present invention, and holds that working tip at an angle to the longitudinal axis of jaw 305 of the instrument. Squeezing handles 307 acts to open the jaws 309 of the instrument.

In another aspect of the present invention, the driver may be modified so that there is a flexible outer collar wrapping around a flexible tube to allow the flexible tube to bend in any radius. Preferably, the flexible outer collar has a longitudinal slot running end-to-end that allows the collar to snap onto the flexible tube. This allows the flexible tube to bend in any radius.

Figure 7:
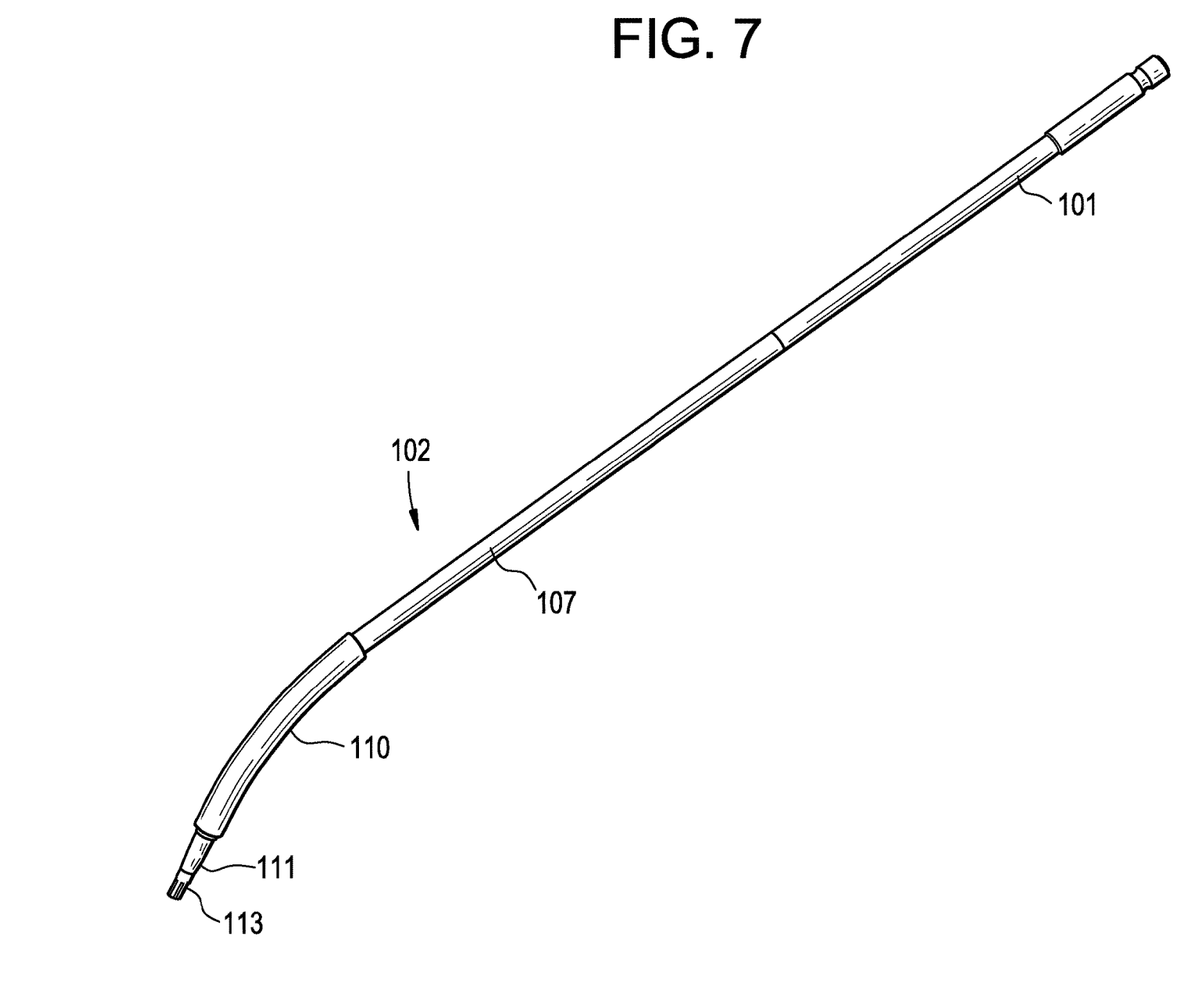
FIGS. 7-9 disclose alternate embodiment of the driver of the present invention.
Figure 8:
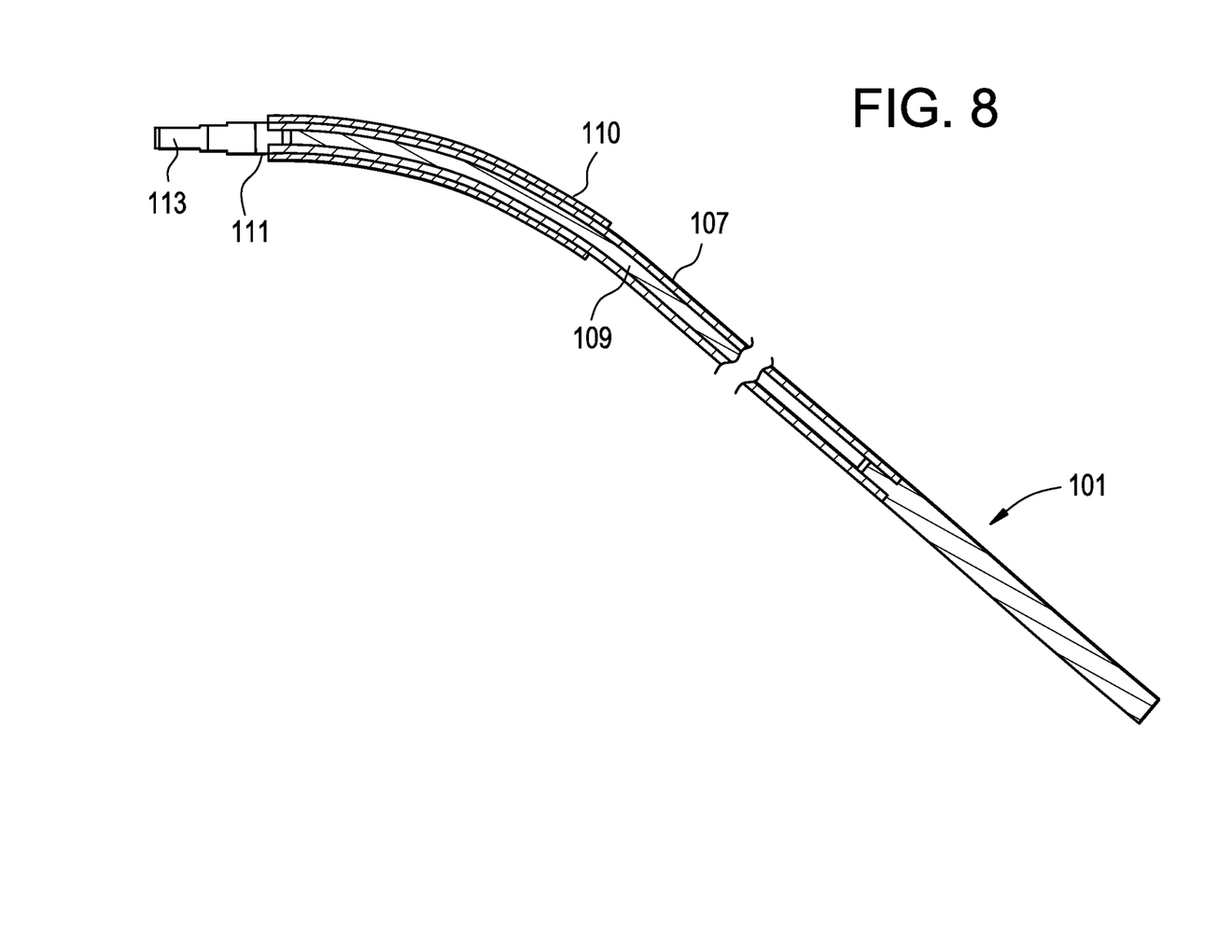

Therefore, in accordance with the present invention, and now referring to FIGS. 7-8, there is provided a flexible bone screw driver comprising:
  a) a rigid proximal portion 101 adapted for connection to a handle or a drill,
  b) an intermediate shaft 102 comprising:
    i) a flexible tube 107 having a bore 108, and
    ii) an inner flexible rod 109 extending through the bore of the flexible tube, and
    ii) an outer malleable collar 110 wrapping around at least a portion of the flexible tube, the collar extending at an angle in an unloaded condition and having a longitudinal slot therein, and
  c) a distal portion 111 having a working tip 113,
wherein the proximal portion is connected to the intermediate shaft, and
wherein the distal portion of the driver is connected to the intermediate shaft.

In some embodiments, flexible tube 107 comprises a plurality of rigid interlocking segments 112, with each segment having a throughbore running therethrough.

Figure 9:
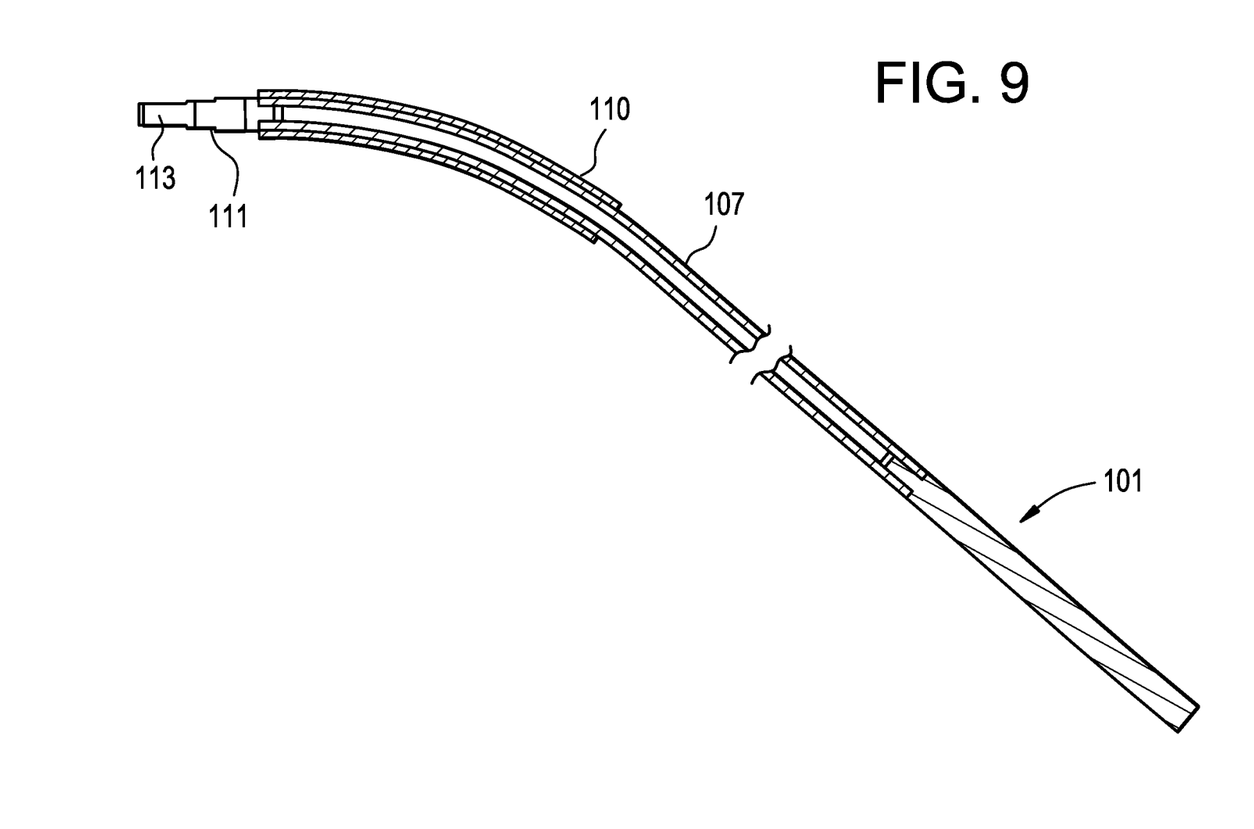

FIG. 9 presents substantially the same driver as FIG. 8, except that the inner flexible rod 109 is missing in FIG. 9.

Although the flexible instrument of the present invention has been presented in a driver application, it is understood that the concepts of the present invention can be applied to other spinal instruments challenged by off-angle orientations, including drills, shavers and rasps.

While this invention has been particularly shown and described with references to preferred embodiments thereof, it will be understood by those skilled in the art that various changes in form and details may be made therein without departing from the scope of the invention encompassed by the appended claims.

I claim:

1. A flexible spinal instrument comprising:
   a) a proximal portion adapted for connection to a handle or a drill,
   b) an intermediate shaft comprising:
      i) a plurality of interlocking segments, each segment having a throughhole, and
      ii) a malleable rod extending through the throughhole of each segment, and
   c) a distal portion having a solid, lumen-free working tip,
   d) a bone screw attached to the working tip,
   wherein the working tip is attached only to a distalmost interlocking segment,
   wherein the working tip has a diameter that is less than a diameter of the distalmost interlocking segment,
   wherein the malleable rod has a pre-determined pre-bent angle in its unloaded condition, thereby pre-determining the trajectory of the tip and facilitating the appropriate and desired insertion angle of a screw into a drill guide without increasing the amount of tissue retraction,
   wherein the malleable rod is the only component extending through the throughhole of each segment.

2. The spinal instrument of claim 1 wherein the proximal portion comprises a rigid tube, and the flexible rod extends into the rigid tube.

3. The spinal instrument of claim 1 wherein the proximal portion comprises a solid rigid rod.

4. The spinal instrument of claim 1 wherein the distal portion is connected to a distalmost interlocking segment.

5. The spinal instrument of claim 1 wherein the malleable rod comprises a polymer.

6. The spinal instrument of claim 1 wherein the malleable rod comprises a memory metal.

7. The spinal instrument of claim 6 wherein the memory metal rod is connected to the distal portion of the spinal instrument.

8. The spinal instrument of claim 6 wherein the memory metal rod is connected to the distal and proximal portions of the spinal instrument.

9. The spinal instrument of claim 6 wherein the memory metal rod is connected to neither of the distal and proximal portions of the spinal instrument.

10. The spinal instrument of claim 1 wherein the malleable rod floats with the plurality of interlocking segments.

11. The spinal instrument of claim 1 wherein the malleable rod has a distal bearing surface.

12. The spinal instrument of claim 1 wherein the working tip is adapted to drill a hole.

13. The spinal instrument of claim 1 wherein the instrument is a screwdriver.

14. The spinal instrument of claim 1 having a first substantially linear configuration and a second deformed configuration, wherein the second deformed configuration allows rotation of the shaft and an application of force along an axis of the working tip.

15. The spinal instrument of claim 1 wherein the distalmost of the interlocking segments has a transverse throughhole.

16. The spinal instrument of claim 1 wherein the working tip tapers distally.

* * * * *